United States Patent
Lee

(10) Patent No.: US 6,736,781 B2
(45) Date of Patent: May 18, 2004

(54) ULTRASOUND IMAGING OF BREAST TISSUE USING ULTRASOUND CONTRAST AGENT

(75) Inventor: Roberta Lee, Redwood City, CA (US)

(73) Assignee: Manoa Medical, Inc., Redwood City, CA (US)

( * ) Notice: Subject to any disclaimer, the term of this patent is extended or adjusted under 35 U.S.C. 154(b) by 0 days.

(21) Appl. No.: 10/167,017

(22) Filed: Jun. 11, 2002

(65) Prior Publication Data

US 2003/0105402 A1 Jun. 5, 2003

Related U.S. Application Data

(60) Provisional application No. 60/322,634, filed on Sep. 12, 2001.

(51) Int. Cl.[7] .................................................. A61B 8/14
(52) U.S. Cl. ................................................... 600/458
(58) Field of Search ................. 600/407–471, 600/560, 567; 604/10, 19, 22, 34, 41, 96, 113, 114, 500; 606/27–32, 35, 38, 41, 159, 167, 170, 171; 607/122; 514/169, 180; 424/9.51, 9.52, 489; 73/620, 625, 626

(56) References Cited

U.S. PATENT DOCUMENTS 5,709,206 A   1/1998   Teboul
6,444,192 B1 *  9/2002   Mattrey ..................... 424/9.52

FOREIGN PATENT DOCUMENTS

| WO | WO 99 32034 A | 7/1999 |
| WO | WO 00/76555 A1 | 12/2000 |
| WO | WO 01 12071 A | 2/2001 |
| WO | WO 01 66016 A | 9/2001 |

* cited by examiner

*Primary Examiner*—Ali M. Imam
(74) *Attorney, Agent, or Firm*—Jung-hua Kuo

(57) ABSTRACT

A system and method for ultrasound imaging of breast tissue by injecting an ultrasound contrast agent into a duct lumen of a patient's breast to enhance the imaging of one or more ducts within a specified lobe of the breast to improve characterization of a lesion or lesions within the duct system of the specified lobe are disclosed. The ultrasound contrast agent used to improve breast imaging may be injected into the duct lumen through an orifice on the nipple and/or a duct wall into the duct lumen. The ultrasound contrast agent may be injected prior to and/or during ultrasound imaging. The ultrasound contrast agent may be an acoustically detectable gas such as a halogenated hydrocarbon, halogenated alkane gases, nitrogen, helium, argon and/or xenon. The halogenated alkane gas may be a perfluorinated hydrocarbon such as saturated perfluorocarbon, unsaturated perfluorocarbon, and/or cyclic perfluorocarbon. The acoustically detectable gas may alternatively be mixed in a liquid solution.

17 Claims, 1 Drawing Sheet

ULTRASOUND IMAGING OF BREAST TISSUE USING ULTRASOUND CONTRAST AGENT

CROSS REFERENCE TO RELATED APPLICATIONS

This application claims priority to U.S. Provisional Patent Application Serial No. 60/322,634, entitled "Tissue Severing and Removal Devices and Methods," filed on Sep. 12, 2001 and is incorporated by reference in its entirety herein.

BACKGROUND OF THE INVENTION

1. Field of the Invention

The present invention relates generally to ultrasound imaging using an ultrasound contrast agent. In particular, a system and method for ultrasound imaging of breast tissue by injecting an ultrasound contrast agent into a duct lumen of a patient's breast to enhance the imaging of one or more ducts within a specified lobe of the breast to improve characterization of a lesion or lesions within the duct system of the specified lobe are disclosed.

2. Description of Related Art

Surgery plays an important role in the diagnosis and treatment of cancer. In the case of breast cancer, surgery comprises a critical component of medical care where early diagnosis and treatment have demonstrated a significant improvement in survival.

Currently the surgical treatment of a breast cancer does not consider anatomical boundaries within the breast. Anatomical boundaries are, however, important in considering the mechanism of cancer spread within the breast. The breast consists of 15 to 20 lobes that begin centrally beneath the nipple-areolar complex and extend in a radial pattern to the periphery of the gland. Milk is produced in numerous small lobules that connect to each main duct. Breast cancer begins in the epithelial cells of the smaller branching ducts entering the lobules. The cancerous cells may multiply and spread within the ducts of the involved lobe and/or may multiply and form a defined mass. Cancerous spread within the ducts is not appreciated by mammography unless microcalcifications are present. Extension within the ducts may also be missed on pathological examination of the specimen unless a sample slice is taken exactly at the level of the involved duct. These limitations using current methods of lumpectomy and examination of the specimen may lead to inadequate surgical treatment of the cancer.

An ultrasound examination of the internal breast anatomy as described in U.S. Pat. No. 5,709,206 to Teboul, incorporated by reference herein, can be utilized to study the lesion and its relation to the lobe in which it is contained. By using axial ductal ultrasound scanning, identification of the affected lobe, lesion size, position within the lobe, and the possibility of other lesions within the affected lobe (e.g. multifocal cancer), and/or spread within the ducts can be delineated prior to surgical treatment.

Duct systems and small lesions within the duct system may be difficult to identify due to limitations of resolution of the ultrasound machine. Thus, there is a need for an improved method for ultrasound imaging of breast tissue to better image one or more ducts within a specified lobe of the breast to improve characterization of lesion or lesions within the duct system of the specified lobe. The improved method for ultrasound imaging would ideally facilitate more accurate diagnosis and surgical excision of lesion or lesions within the duct system of the specified lobe.

SUMMARY OF THE INVENTION

A system and method for ultrasound imaging of breast tissue by injecting an ultrasound contrast agent into a duct lumen of a patient's breast to enhance the imaging of one or more ducts within a specified lobe of the breast to improve characterization of a lesion or lesions within the duct system of the specified lobe are disclosed. It should be appreciated that the present invention can be implemented in numerous ways, including as a process, an apparatus, a system, a device, or a method. Several inventive embodiments of the present invention are described below.

In one preferred embodiment, an improved method for ultrasound imaging of breast tissue using an ultrasound contrast agent to enhance the imaging of one or more ducts within a specified lobe of the breast to improve characterization of a lesion or lesions within the duct system of the specified lobe is disclosed. The method may help determine whether removal of the lesion requires excision of part of the lobe, the entire lobe, or the entire lobe plus surrounding adjacent tissue. The ultrasound contrast agent is injected into a duct lumen by injecting through a duct orifice on a nipple and/or through a duct wall into a duct lumen. In addition, the ultrasound contrast agent is injected into the duct lumen before and/or during ultrasound imaging.

These and other features and advantages of the present invention will be presented in more detail in the following detailed description and the accompanying figures which illustrate by way of example the principles of the invention.

BRIEF DESCRIPTION OF THE DRAWINGS

The present invention will be readily understood by the following detailed description in conjunction with the accompanying drawing, wherein like reference numerals designate like structural elements, and in which.

DESCRIPTION OF SPECIFIC EMBODIMENTS

Figure 1:
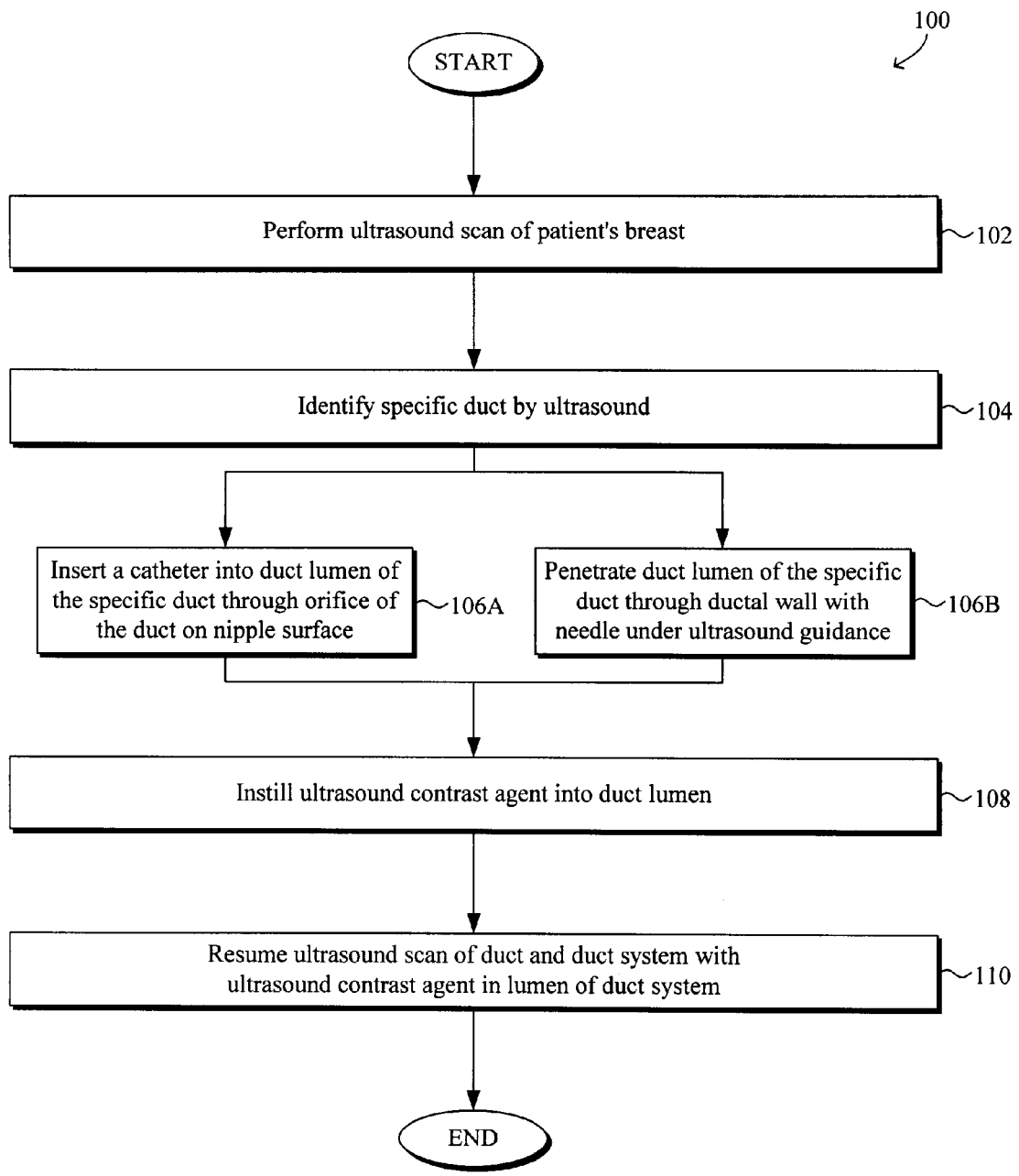
FIG. 1 is a flowchart illustrating a method for ultrasound imaging of breast tissue by injecting an ultrasound contrast agent into a duct lumen.

A system and method for ultrasound imaging of breast tissue by injecting an ultrasound contrast agent into a duct lumen of a patient's breast to enhance the imaging of one or more ducts within a specified lobe of the breast to improve characterization of a lesion or lesions within the duct system of the specified lobe are disclosed. The following description is presented to enable any person skilled in the art to make and use the invention. Descriptions of specific embodiments and applications are provided only as examples and various modifications will be readily apparent to those skilled in the art. The general principles defined herein may be applied to other embodiments and applications without departing from the spirit and scope of the invention. Thus, the present invention is to be accorded the widest scope encompassing numerous alternatives, modifications and equivalents consistent with the principles and features disclosed herein. For purpose of clarity, details relating to technical material that are known in the technical fields related to the invention have not been described in detail so as not to unnecessarily obscure the present invention.

Ultrasound imaging is employed to determine the location of a lesion within a selected region of a patient's breast and/or help guide a surgical procedure. It is noted that any suitable ultrasound imaging modality may be employed with ultrasound contrast agent, including but not limited to ultrasound and three-dimensional ultrasound. Ultrasound or three-dimensional ultrasound can delineate the internal anatomy of the breast and can produce near real-time or actual real-time imaging. The ultrasound imaging may comprise radial scanning and/or axial ductal ultrasound scanning. The ultrasound imaging may be employed to produce a three-dimensional image.

As described in co-pending U.S. patent application No. 10/097,412 by Lee et al., entitled "Devices and Methods for Tissue Severing and Removal," filed on Mar. 12, 2002, and incorporated by reference herein, a tissue severing device facilitates in severing and removing a mass of tissue such as a lesion from a selected region of a patient's breast. The use of the tissue severing device is preferably performed in relation to the internal anatomy of the breast and more specifically to excise part of a lobe, an entire lobe, or an entire lobe with adjacent tissue. The ultrasound imaging using ultrasound contrast agent may facilitate in such tissue severing procedures performed in relation to the internal anatomy of the breast and performed to excise part of a lobe, an entire lobe, or an entire lobe with adjacent tissue.

The improved ultrasound imaging method 100 using ultrasound contrast agent enhances ultrasound imaging of the internal breast anatomy, particularly the lobar structure or the ducts within the lobe. FIG. 1 is a flowchart illustrating a method 100 for ultrasound imaging of breast tissue by injecting an ultrasound contrast agent into a duct lumen. At step 102, an ultrasound scan of the patient's breast is performed. At step 104, a specific duct is identified while performing the ultrasound scan of step 102.

Next, a transport mechanism such as a catheter or a needle for instilling or injecting ultrasound contrast agent into the specific duct identified in step 104 is inserted in the duct lumen. For example, a catheter may be inserted into the duct lumen through an orifice of the duct on the surface of the nipple as shown at step 106A. Alternatively, a needle may be inserted into the patient's breast so as to penetrate the duct lumen, preferably under the guidance of the ultrasound scan of step 102 still being performed, as shown at step 106B.

At step 108, the ultrasound contrast agent is instilled or injected into the duct lumen through the transport mechanism, e.g., catheter or needle. At step 110, the ultrasound scan continues or resumes with scanning of the duct and/or the duct system having ultrasound contrast agent within the lumen of the duct system.

It is to be understood that ultrasound imaging optionally can be performed during insertion of the transport mechanism into the duct lumen and/or during injection of the ultrasound contrast agent. In addition, steps 104–110 of the improved ultrasound imaging method 100 may be repeated so as to perform the ultrasound scanning on multiple ducts and/or to repeat the ultrasound scanning on the same duct.

The ultrasound contrast agent may be an acoustically detectable gas such as one selected from halogenated hydrocarbon, halogenated alkane gases, nitrogen, helium, argon, and xenon. Perfluorinated hydrocarbon represents a preferred halogenated alkane gas for its acoustic properties as well as its low toxicity. Perfluorinated hydrocarbon may be a saturated perfluorocarbon, an unsaturated perfluorocarbon, and/or a cyclic perfluorocarbon. The ultrasound contrast agent may alternatively be an acoustically detectable gas mixed in a liquid solution.

It is noted that while the ultrasound imaging method using ultrasound contrast agent described herein is generally useful for procedures in soft tissue, the ultrasound imaging method is particularly effective in providing precise control during the excision of a lesion or abnormality in breast tissue with minimal invasiveness.

It is to be understood that various other features may be provided in the tissue severing device. For example, locking mechanisms may be provided to ensure a greater degree of control over the spatial relationship between the cutting tool and the guide. In addition, the device may be manually, automatically, and/or remotely controlled.

All patents, patent applications, and publications referenced herein are hereby incorporated by reference in their entireties.

While the preferred embodiments of the present invention are described and illustrated herein, it will be appreciated that they are merely illustrative and that modifications can be made to these embodiments without departing from the spirit and scope of the invention. Thus, the invention is intended to be defined only in terms of the following claims.

What is claimed is:

1. In a method for ultrasound imaging of breast tissue, the improvement which comprises injecting an ultrasound contrast agent into a duct lumen of a milk duct of a human patient's breast, wherein the ultrasound imaging using ultrasound contrast agent at least one of facilitates diagnosis of the milk duct and simultaneously guides a surgical procedure involving the specific duct.

2. The method of claim 1, wherein the ultrasound contrast agent is injected into the duct lumen through at least one of an orifice on the nipple and a duct wall into the duct lumen.

3. The method of claim 1, wherein the ultrasound contrast agent is injected at least one of prior to and during ultrasound imaging.

4. The method of claim 1, wherein the ultrasound contrast agent is an acoustically detectable gas.

5. The method of claim 4, wherein the acoustically delectable gas is a halogenated hydrocarbon.

6. The method of claim 4, wherein the acoustically detectable gas is selected from the group consisting of halogenated alkane gases, nitrogen, helium, argon and xenon.

7. The method of claim 4, wherein the halogenated alkane gas is a perfluorinated hydrocarbon selected from the group consisting of saturated perfluorocarbon, an unsaturated perfluorocarbon, and a cyclic perfluorocarbon.

8. The method of claim 4, wherein the acoustically detectable gas is mixed in a liquid solution.

9. A method, comprising the steps of:
 performing an ultrasound scan of human patient's breast;
 identifying a specific milk duct of the breast;
 injecting an ultrasound contrast agent into a duct lumen of the specific milk duct; and
 performing an ultrasound scan of the specific milk duct after the injecting to at least one of facilitate diagnosis of the specific milk duct and to simultaneously guide a surgical procedure involving the specific milk duct.

10. The method of claim 9, wherein the step of injecting comprises inserting a catheter into the duct lumen of the specific duct through an orifice of the duct on a surface of a nipple of the breast.

11. The method of claim 9, wherein the step of injecting comprises inserting a nipple into the duct lumen of the specific duct under ultrasound guidance.

12. The method of claim 9, wherein the ultrasound contrast agent is injected at least one of prior to and during ultrasound imaging.

13. The method of claim 9, wherein the ultrasound contrast agent is an acoustically detectable gas.

14. The method of claim 13, wherein the acoustically detectable gas is a halogenated hydrocarbon.

15. The method of claim 13, wherein the acoustically detectable gas is selected from the group consisting of halogenated alkane gases, nitrogen, helium, argon and xenon.

16. The method of claim 15, wherein the halogenated alkane gas is a perfluorinated hydrocarbon selected from the group consisting of saturated perfluorocarbon, an unsaturated perfluorocarbon, and a cyclic perfluorocarbon.

17. The method of claim 13, wherein the acoustically detectable gas is mixed in a liquid solution.

* * * * *